(12) United States Patent
Velazquez Pereda et al.

(10) Patent No.: US 8,709,455 B2
(45) Date of Patent: Apr. 29, 2014

(54) SERICIN CATIONIC NANOPARTICLES FOR APPLICATION IN PRODUCTS FOR HAIR AND DYED HAIR

(75) Inventors: Maria Del Carmen Velazquez Pereda, Sãn Paulo (BR); Marcio Antonio Polezel, Indaiatuba (BR); Gustavo de Campos Dicamant, Sorocaba (BR); Cecilia Nogueira, Sorocaba (BR); Amanda Gomes Marcelino, Campinas (BR); Marcos Roberto Rossan, Sorocaba (BR); Maria Helena Andrade Santana, Campinas (BR)

(73) Assignee: Chemyunion Quimica Ltda., Sorocaba (BR)

(*) Notice: Subject to any disclaimer, the term of this patent is extended or adjusted under 35 U.S.C. 154(b) by 0 days.

(21) Appl. No.: 13/378,583

(22) PCT Filed: Jun. 15, 2009

(86) PCT No.: PCT/IB2009/052540
§ 371 (c)(1),
(2), (4) Date: Mar. 13, 2012

(87) PCT Pub. No.: WO2010/146415
PCT Pub. Date: Dec. 23, 2010

(65) Prior Publication Data
US 2012/0164196 A1 Jun. 28, 2012

(51) Int. Cl.
| A61K 8/02 | (2006.01) |
| A61K 8/00 | (2006.01) |
| A61K 8/18 | (2006.01) |
| A61Q 5/08 | (2006.01) |
| A61Q 19/02 | (2006.01) |
| A61K 8/64 | (2006.01) |
| A61K 8/65 | (2006.01) |

(52) U.S. Cl.
USPC .......................... 424/401; 424/62; 424/70.14

(58) Field of Classification Search
USPC ....................................................... 424/401
See application file for complete search history.

(56) References Cited

U.S. PATENT DOCUMENTS

| 4,839,165 A | 6/1989 | Hoppe et al. |
| 4,839,168 A | 6/1989 | Abe et al. |
| 6,197,318 B1 | 3/2001 | Abe et al. |
| 7,060,260 B2 | 6/2006 | Fahnestock et al. |
| 2004/0170590 A1 | 9/2004 | Fahnestock et al. |
| 2007/0041925 A1 | 2/2007 | Picano et al. |
| 2008/0003295 A1 | 1/2008 | Bosch et al. |
| 2008/0141792 A1 | 6/2008 | Li et al. |
| 2010/0047202 A1* | 2/2010 | Goddinger et al. ........ 424/70.12 |

FOREIGN PATENT DOCUMENTS

| DE | 32 33 388 A1 | 3/1984 |
| DE | 10240757 A1 | 7/2003 |
| DE | 10333253 A1 | 2/2005 |
| GB | 888625 A | 1/1962 |
| JP | 2000-191446 A | 7/2000 |
| JP | 2000-290143 A | 10/2000 |
| JP | 2002-284635 A | 10/2002 |
| JP | 2004-238356 A | 8/2004 |
| JP | 2005-068059 A | 3/2005 |
| JP | 2006-149510 A | 6/2006 |
| JP | 2007-015936 A | 1/2007 |
| JP | 2007-204376 A | 8/2007 |
| JP | 2008-174516 A | 7/2008 |
| JP | 2008-208123 A | 9/2008 |
| JP | 2008-266235 A | 11/2008 |
| JP | 2008-273907 A | 11/2008 |
| KR | 2002/0094646 A | 12/2002 |
| WO | 2004/024176 A1 | 3/2004 |
| WO | 2004/073644 A2 | 9/2004 |
| WO | WO 2008077683 A2 * | 7/2008 |

OTHER PUBLICATIONS

Scientific Committee on Consumer Products (SCCP). "Opinion on Alkyl (C16, C18, C22) Trimethylammonium Chloride for other uses than as a preservative," (2007), http://ec.europa.eu/health/scientific_committees/consumer_safety/docs/sccs_o_012.pdf, accessed on May 31, 2012.*
Woodruff, John. "Hair Care 2008," (2008). SPC, https://docs.google.com/viewer?a=v&q=cache:pz9V5Ei-UxwJ:www.creative-developments.co.uk/pages/pres/new/29.pdf+seriseal+complex&hl=en&gl=us&pid=bl&srcid=ADGEESiDrjiGU_fhiU0GM6lgAP8DoBmarR2UfjOznSpUV8BTxByP8n4zmFieeudSpuppYm-Gb9w0bfhh9JJzyJXT9jlv6gz0mnDljTShtXgztaawW_3-clvSRXr9zUmlaMWrN2nvf46r&sig=AHIEtb.*
Continuation of (V): accessed on May 31, 2012.*
International Search Report of PCT/IB2009/052540, mailing date Apr. 30, 2010.

* cited by examiner

Primary Examiner — Robert T Crow
Assistant Examiner — Doan Phan
(74) Attorney, Agent, or Firm — Westerman, Hattori, Daniels & Adrian, LLP (57) ABSTRACT

The objective of this patent application is the application/use of sericin nanoparticles m cosmetic formulas for hair care, as an agent that bestows/gives gloss and softness and promotes maintenance of coloration in dyed hair.

7 Claims, 6 Drawing Sheets

● P<0.001 in relation to placebos at the same concentrations and in relation to the control. Therefore, the reduction in volume is statistically significant.

▲ P<0.01 in relation to the control, indicating less statistical significance.

Figure 6

(a) Virgin Hair (b) Hair Damaged by decoloration (c) Hair Damaged by discoloration (d) Hair treated with sericin cationic nanoparticles

SERICIN CATIONIC NANOPARTICLES FOR APPLICATION IN PRODUCTS FOR HAIR AND DYED HAIR

FIELD OF THE INVENTION

This patent intents the use of sericin cationic nanoparticles as an active ingredient for the care of damaged hair and maintenance of color in dyed hair.

Additionally, the present patent invention is related to the use of sericin cationic nanoparticles obtained from the reticulation between sericin protein, extracted from *Bomby mori* silkworm cocoons, with quaternized guar gum and, coated with at least one cationic surfactants. These nanoparticles were dispersed in a medium containing cationic polymer.

PRIOR ART

Claiming the use of sericin as hair conditioning agent, some products have been developed:

U.S. Pat. No. 4,839,165: Water-based cosmetic agent for hair which contains sericin and pelargonic acid as active ingredients U.S. Pat. No. 4,839,168: Hair cosmetic compositions comprise (A) an extract obtained by polar solvent extraction of a plant, preferable ones of which are birch, rosemary and hamamelis, and (B) a polypeptide compound including keratin, keratin derivative, silk and hydrolysate of silk.

U.S. Pat. No. 6,197,318: A composition for external use which contains xyloglucan. It preferably further contains an ultraviolet shielding agent, a thickening polysaccharide, a thickening polysaccharide and sericin, a carboxyvinylpolymer, or an alkyl-modified carboxyvinylpolymer. The external-use compositions may be processed into products comprising a variety of cosmetics, including hair-care products such as shampoos, rinses and hair-dyes.

U.S. Pat. No. 7,060,260: Skin care, hair care and hair coloring compositions comprising a water-soluble spider silk protein as an active ingredient are described. The water-soluble silk protein deposits onto the skin or the natural hair keratin to provide a smooth and durable film to provide added strength for protection against environmental, chemical, and grooming associated damage.

US 2007/0041925A1: Cosmetic preparations, especially hair care preparations or hair care products, containing protein hydrolysates of silk, pashmina, cashmere wool, merino wool and/or mohair, mussel thread extracts, so-called bysuss threads, and sericin and/or sericin hydrolysates. The preparations are mild for skin and hair and lead to an improvement of hair structure and physical-optical hair properties.

GB 888626 (A): Compositions for the treatment of the hair comprise sericin and a carrier therefore, the active material preferably amount to 0.1 to 1% by weight of the composition.

DE 3233388 (A1): The invention relates to hair cosmetic compositions and cosmetic bath additives containing sericin. These compositions display when used besides a substantive behaviour towards human hair and human skin a pronounced skin-smoothing effect.

JP2008273907(A): To provide a cosmetic for hair dressing, having excellent setting ability, high in moisture resistance of curl retention and forming a natural hair style giving natural feeling. This hair cosmetic is compounded with 0.001-5 wt. % sericin. Wherein, the sericin is solubilized with a specific anionic surfactant.

JP 2008174516 (A): To provide a composition for foamy hair cosmetics that exhibits excellent foamability and foam retention, exhibits excellent effects of imparting tightness to hair and preventing hair damages and is excellently safe. The composition for this foamy hair cosmetics comprises water and dissolving therein, (A) a hydrolyzate of sericin, (B) a decomposate of keratin, and (C) ethanol JP 2007204376 (A): To obtain a composition that controls swelling of the hair damaged by hair dyeing, permanent wave treatment, etc., in a wet state, prevents elution of lipid and protein from the inside of the hair and prevents the progress of hair damage. The swelling control composition for the hair comprises (A) a sericin having 5,000-20,000 average molecular weight and (B) a vegetable protein hydrolysate having 200-2,000 average molecular weight.

JP 2007015936 (A): To obtain a hair cosmetic that suppresses hair swelling, prevents elution of protein inside the hair, controls roughness and dryness of the hair even under a dry environment, improves setting properties and wiriness and has high care effect on the damaged hair. This hair cosmetic comprises a sericin having 5,000-20,000 number-average molecular weight.

JP 2006149510 (A): Obtain a hair tint composition containing silk and wool proteins having a low molecular weight is provided which dyes hair uniformly and protects hair from damage, as compared to conventional hair tints. A hair tint composition contains 0.5 to 5.0% by weight of each of silk protein and wool protein having a molecular weight of 100 to 900, based on the total weight of the composition.

JP 2005068059 (A): To provide a hair treatment preparation being of two-part type, comprises a 1st liquid consisting of an aqueous solution containing a sericin hydrolyzate with a mass-average molecular weight of 30,000-70,000 and a compound having two amino groups and a 2nd liquid consisting of an aqueous buffer solution containing transglutaminase.

DE 10333253 (A1): cosmetic formulas and colorants for keratin fibers, used for cleaning and/or conditioning skin and hair and restructurizing and coloring keratin fibers, especially human hair, contain a complex of sericin and fibroin and/or derivatives.

JP 2004238356 (A): To obtain a hair-treating agent capable of finishing the hair so as to have smooth and moisten feelings, keeping natural gloss and volume feeling for a long time. This hair-treating agent comprises (a) one or more kinds of compounds selected from silk proteins or their hydrolyzed products and derivatives thereof, fibroin and sericin and others.

DE 10240757 (A1): Cosmetic composition used for cleaning and/or caring for skin and hair comprises sericin and fibroin and/or their hydrolyzates and/or derivatives JP 2002284635 (A): To provide a hair treating agent ameliorating injured hairs and imparting gloss, suppleness and smoothness to the hair, and to provide a method of treating hair that improves gloss, suppleness and smoothness of the hair using the hair treating agent. This agent comprises a hydrolyzed silk or its derivative, carboxymethyl chitin and sericin.

JP 2002284635 (A): To provide a fixer for a coloring agent or an agent for hair shape retention to be compounded in the external skin preparation. This preparation comprises a high molecular weight sericin having an average molecular weight of 70,000 to 300,000.

JP 2000290143 (A): To obtain a hair cosmetic capable of imparting tensity, stiffness and a voluminous feeling to hair damaged, weakened and softened by a chemical treatment such as perming, bleaching or hair coloring or naturally slender and soft hair and having excellent styling properties. This hair cosmetic comprises, a solubilized silk peptide (a polypeptide, etc., consisting essentially of sericin) and/or a water=soluble chitosan derivative (hydroxyethylchitosan, etc.), etc.

JP 2000191446 (A): To obtain the subject hair cosmetic that shows excellent strengthening and repairing action on damaged and hardened hairs with changed hair protein structure by treatment with chemicals or the like and gives the hairs flexibility and gives excellent styling action to the hair by using a solubilized silk peptide and sugar alcohol or the like in the hair cosmetic. This cosmetic can be widely applied in a variety of production form, for example, solutions, foams, sprays or the like.

WO/2004/024176: Cosmetic preparations containing a synergistically effective active substance complex made of sericine and fibroin and/or the derivatives thereof for the treatment of skin and hair.

US 2008/0003295: Bioadhesive nanoparticulate compositions, comprising active agent particles and one or more cationic surface stabilizers, are described. The particles may consist of pharmacologically active compounds (e.g., drug compounds for human or veterinary use), cosmetic agents, etc.

BRIEF DESCRIPTION OF THE INVENTION

Human Hair

Hair fibers, which are structures derived of the epidermis, have between 50-100 µm of diameter and are made of cuticle and cortex and, in some cases, medulla in the central region. All of these are composed by dead cells, filled essentially with the keratin protein.

The cortex is the largest part in volume and contributes mainly with the mechanical and color properties of hair. It consists of shaft shaped cells, closely packed, filled with keratin filaments, which are oriented parallel to the longitudinal axis of the hair.

The cuticle consists of six to eight layers of overlapped flattened cells and has significant influence in the hair's appearance. In virgin hair the cuticle has smooth appearance which allows reflection of light. It reduces friction between each hair strand, being responsible for the gloss and texture of hair. Damages to the cuticle may be caused by the mechanical friction during brushing and/or high hairdryer temperature.

The hair surface has anionic character due to the presence of sulphonate and carboxyl groups in the proteins and lipids components of its fibers. When hair is exposed to ultraviolet radiation or bleached with hydrogen peroxide, the Bisulfate bridges present in cysteine are oxidized to sulfonate. The concentration of such negative charges may vary along the surface of the hair due to chemical treatments or exposure to environmental factors such as ultraviolet radiation. Such variation is a factor that can affect the adsorption of cationic compounds on the hair surface.

Currently, there is great need to treat the weakened or damaged hair resulting from chemical treatments such as discoloration, dyes and smoothing. Thereby, one of the major challenges of the cosmetics industry is to innovate releasing hair conditioning products that can provide substantiveness with high efficiency in cuticle repair, resulting in improvement of sensory effects, such as brightness and softness, reducing the volume of hair, and products that contribute to the maintenance of the color of dyed hair.

Hair Conditioning

The hair conditioning is the opposite of cleaning. In contrast to the shampoos, involving the removal of material from the surface of the hair, the conditioning is putting back due amounts of proper ingredients. While the shampoo relies on the action of anionic materials, the hair conditioning requires the use of materials that are different in aspects such as ionic character, surface properties and solubility characteristics.

With hair conditioning, a feeling of softness, tenderness and ease of combing is expected. The effective conditioning agents are generally cationic and much less soluble in water. The most commonly used are quaternary ammonium compounds, cationic polymers, and silicone oils. The substantiveness of cationic materials is due to the strong interaction between its positive charges and the negatively charged surface of the hair The Sericin The silk derived from silkworm *Bombyx mori* consists mainly of proteins sericin and fibroin. Sericin constitutes about 25-30% of the silk protein and involves the fibroin fiber with successive sticky layers that help the formation of the cocoons. Fibroin constitutes 70-80%, and it is the main product of silk processing.

Sericin is a globular protein, soluble in water and has a wide range of molecular weight ranging from 10 to over 300 kDa. It consists of 17 amino acids and among the main are serine (31%), glycine (19.1%), aspartic acid (17.8%), and threonine (8.0%).

The use of sericin as hair care agent is widely studied, as can be seen in the patents cited in the Prior Art item Cationic Agents The cationic agent used in this work for the formation of nanoparticles is the Quaternized Guar gum, a cationic derivative of guar gum. It is a polymer of high molar mass, which provides excellent conditioning properties for skin and hair care products. Used in shampoos, rinse creams, lotions, creams and other personal care products.

The sericin cationic nanoparticles were coated with cetyl-trimethylammonium chloride (CTAC) and behenyl trimethylammonium chloride (BTAC) to change its load surface. These compounds are quaternary ammonium salts and have at least one nitrogen atom, with four alkyl or aryl groups linked to them; they are always cationic regardless of the environment pH and, therefore, are generally incompatible with anionic surfactants. The long alkyl groups promote an improved deposition on the hair, leading to conditioning benefits such as improved softness on dry hair. Therefore, the properties of various derivatives of quaternary ammonium are related to the cationic density and to the number and size of the alkyl chains present in the molecule.

The Poliquatemium 7 contitutes a percentage of the environment in which the coated sericin cationic nanoparticles were dispersed. It is a cationic polymer, widely used in shampoo formulas, which may lead to changes in the surface that vary from formation of a thin protection layer on the hair fibers to synergic action that enhances the performance of other products for the improvement of aspects such as smoothness and ease of combing. Poliquaternium 07 is a cationic copolymer, consisting of acrylamide and diallyldimethyl ammonium chloride. It is used as an antistatic, layer forming and fixing agent in a variety of cosmetics, and considered safe for use in cosmetic products, and is considered safe for use in cosmetic formulas.

One of the major challenges of the cosmetics industry is to innovate with hair conditioning products which can provide substantiveness, with high efficiency in cuticle repair, resulting in improvement of sensory effects, such as brightness and softness, besides reduction of hair volume.

Currently, nanotechnology has been prominent as an alternative for the development and innovation in the cosmetics area, receiving high investments in research and development from companies in the trade. The nanoparticles are particles with sizes in the range between 1 and 1000 nm (approximately) and can be composed of a wide range of materials. In this context, their properties emerge from the set of aggregated molecules and therefore are different from the properties of individual molecules. Due to their size, nanoparticles have a large surface area per volume unit and their surface effects are predominant.

Therefore, considering that: The already known properties of sericin and its wide use in hair and skin care preparation; the growing application of nanotechnology in cosmetic preparations and the capability of cationic materials to adhere to the anionic surface of human hair, we analyzed in this survey the application of sericin cationic nanoparticles coated with cationic surfactants, on the surface of damaged hair, and their action in the reduction of hair volume, gloss and changes in sensorial properties such as smoothness, flexibility, roughness and damage repair. Additionally, the capability of these nanoparticles to contribute for the maintenance of color in dyed hair was also examined.

DETAILED DESCRIPTION OF THE INVENTION

This patent aims at the application of sericin cationic nanoparticles coated with cationic surfactants in hair care products promoting an increase in gloss, reduction in volume, in addition to improving sensorial features as smoothness, flexibility, etc. This patent also aims at the application of these particles in hair dyes for maintenance of color in dyed hair. These properties of nanoparticles were proved by instrumental and sensorial tests, in vitro, with hair locks, as described below.

1. Gloss Tests in Caucasian Hair Locks

The gloss effect in Caucasian virgin hair locks chemically treated by decoloration was evaluated using Glossmeter Novo Gloss® equipment. The evaluated products where (i) sericin cationic nanoparticles dispersed in water at three different concentrations (1%, 3%, 5%) and (ii) placebo solubilized in water at the same three concentrations and composed by the same components of the nanoparticles' formula, except for sericin protein. Locks treated with water only were used as control.

Each lock was immersed in the test products, separately, for 2 minutes Next these locks were combed, dried with cool air and then ten measures of brightness were made in each lock.

The hair gloss effect was analyzed in terms of perceptual increase of gloss, comparing the average values of gloss obtained from control locks to the values obtained from the locks treated with nanoparticles and placebo.

The technique for hair gloss measurement is based on the principle of intensity of reflected light. Hair is lightened under an oblique incident light (at an angle of 85°), and the reflected light is registered in accordance to the angle of observation. The higher reflection, the higher gloss. Reflected light is measured by a detector. The values are expressed in gloss units (GU-0, 1 a 1000). The results were evaluated through statistical analysis using the Tukey-kramer multiple comparison test, to verify the significance degree of gloss increase.

Figure 1:
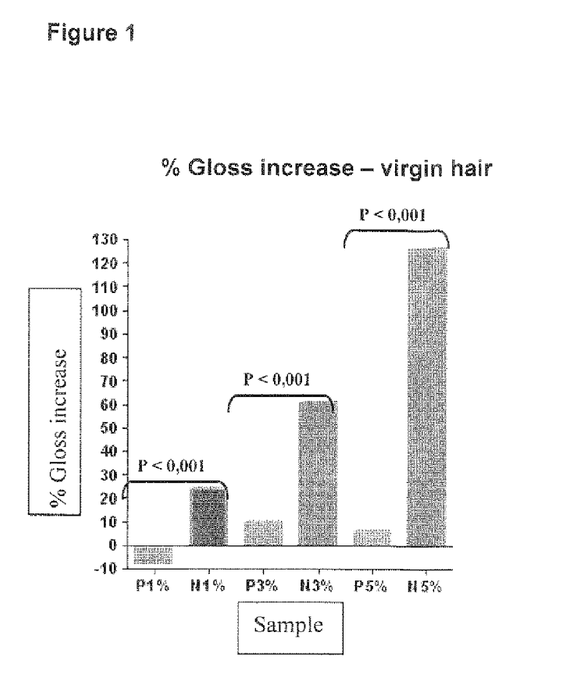
FIG. 1 shows the percentual gloss increase of virgin hair treated with Placebos (P) and with Sericin Cationic Nanoparticles (N) in different concentrations, where (P1%) aqueous placebo solution at 1%, (P3%) aqueous placebo solution at 3%, (P5%) aqueous placebo solution at 5%, (N1%) dispersion of sericin cationic nanoparticles in water at 1%, (N3%) dispersion of sericin cationic nanoparticles in water at 3%, (N5%) dispersion of sericin cationic nanoparticles in water at 5%.
Figure 2:
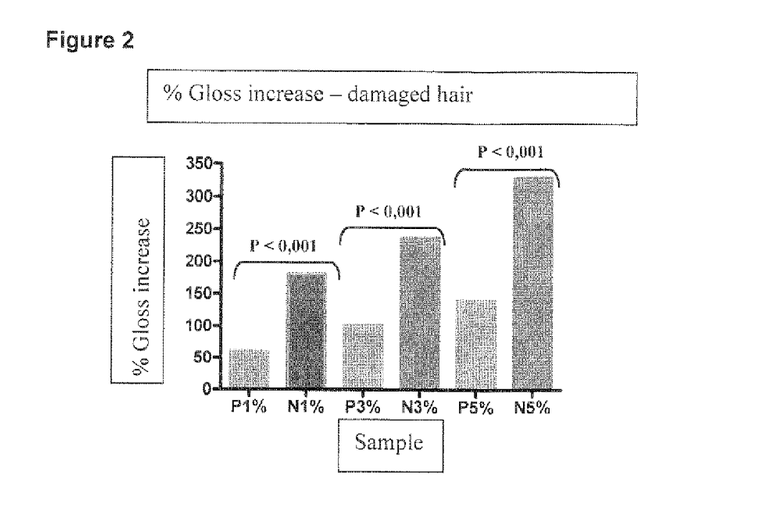
FIG. 2 shows the percentual gloss increase of damaged hair treated with Placebos (P) and with Sericin Cationic Nanoparticles (N) in different concentrations, where (P1%) hair lock treated with aqueous placebo solution at 1%, (P3%) lock treated with aqueous placebo solution at 3%, (P5%) lock treated with aqueous placebo solution at 5%, (N1%) dispersion of sericin cationic nanoparticles in water at 1%, (N3%) dispersion of sericin cationic nanoparticles in water at 3%, (N5%) dispersion of sericin cationic nanoparticles in water at 5%.

FIGS. 1 and 2 present the percentage of gloss increase in virgin and damaged hair obtained by instrumental analysis, resulting from application of sericin nanoparticles and placebo in comparison to the control.

FIG. 1 shows that the gloss of virgin hair promoted by the application of sericin cationic nanoparticles is superior to gloss promoted by the addition of Placebo, at the three studied concentrations.

The statistical analysis shows that the gloss increase promoted by sericin cationic nanoparticles is significant (P<0, 001) when compared to the gloss increase promoted by placebos, at the same concentrations.

FIG. 1 compares the gloss increase obtained in damaged hair treated with sericin cationic nanoparticles and with Placebo, using as reference hair treated with only water. Behold again in this case that the gloss promoted by the application of sericin cationic nanoparticles is superior to gloss promoted by the placebos, at the three studied concentrations. The statistical analysis shows that the gloss increase promoted by sericin cationic nanoparticles is significant (P<0,001) when compared to the gloss increases promoted by placebos, at the same concentrations.

2. Sensorial Effect

The sensorial effect of sericin cationic nanoparticles in hair locks was evaluated by 10 people, through the answer of a specific questionnaire. Caucasian damaged locks were immersed, for 2 minutes, in dispersion of sericin cationic nanoparticles and in water, for comparison. Then these locks were vertically suspended in a holder for removal of excessive water.

The appraisers analyzed the locks while humid and after drying. The locks were numerated so the examiners couldn't have knowledge of the analyzed sample (blind survey). The questionnaire was answered by attributing grades from 1 to 5, where 1 means the less satisfactory and 5, the most satisfactory. The analyzed aspects on the questionnaire were smoothness, ease of combing, perception of appearance improvement and roughness. The results were analyzed in relation to the grades granted by the appraisers.

Figure 3:
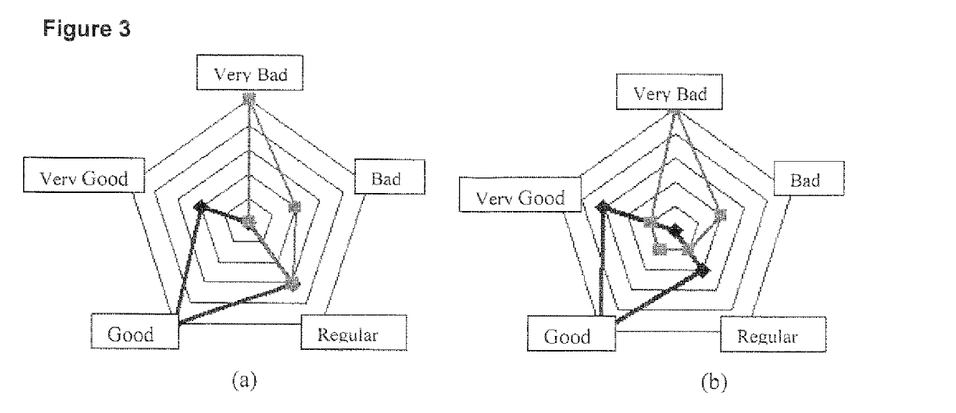
FIG. 3 shows the result of a comparative sensorial analysis for (a) softness and (b) flexibility of untreated hair (pink) and hair treated with sericin cationic nanoparticles (blue).
Figure 4:
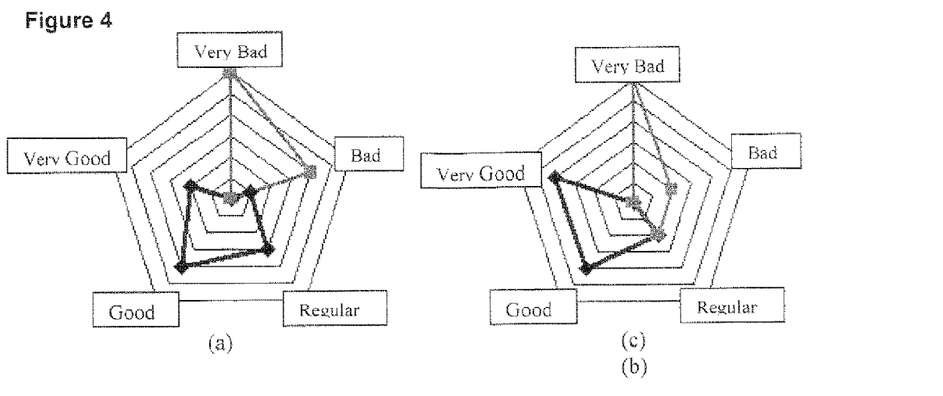
FIG. 4 shows the result of a comparative sensorial analysis for (a) damage improvement and (b) roughness of untreated hair (pink) and hair treated with sericin cationic nanoparticles (blue).

Sensorial analyses are presented in FIGS. 3 and 4. The blues lines refer to hair treated with sericin cationic nanoparticles and the pink lines refer to untreated hair.

FIGS. 3 (a) and (b) presents the results of smoothness and ease of combing, respectively. Behold the remarkable difference between treated and untreated hair, indicating that the sericin cationic nanoparticles grants greater smoothness and facilitates hair combing.

FIG. 4 presents the perception of improvement of damaged hair (a) and hair roughness (b). We can clearly notice the improvement in these two aspects after treatment with sericin cationic nanoparticles.

3. Reduction of Hair Volume

This test's objective was to evaluate the effect of sericin cationic nanoparticles in reduction of volume of hair locks, comparing to hair treated with placebo and hair treated only with water (control).

The afro-American hair locks, damaged by decoloration, were immersed in each product for 2 minutes. Then the locks were combed and suspended vertically in a holder for removal of excessive water, dried with cold air and photographed. The opening of the locks was measured with the software Image Tool.

The evaluated products were (i) sericin cationic nanoparticles dispersed in water at three different concentrations (1%, 3%, 5%) and (ii) placebo solubilized in water at the same three concentrations and composed by the same components of the nanoparticles' formula, except for sericin protein. Locks treated with water only were used as control.

The results were analyzed as to volume reduction of hair locks (in centimeters), and a statistical analysis was made using the Tukey-kramer multiple comparison test to verify the degree of volume reduction in hair locks.

Figure 5:
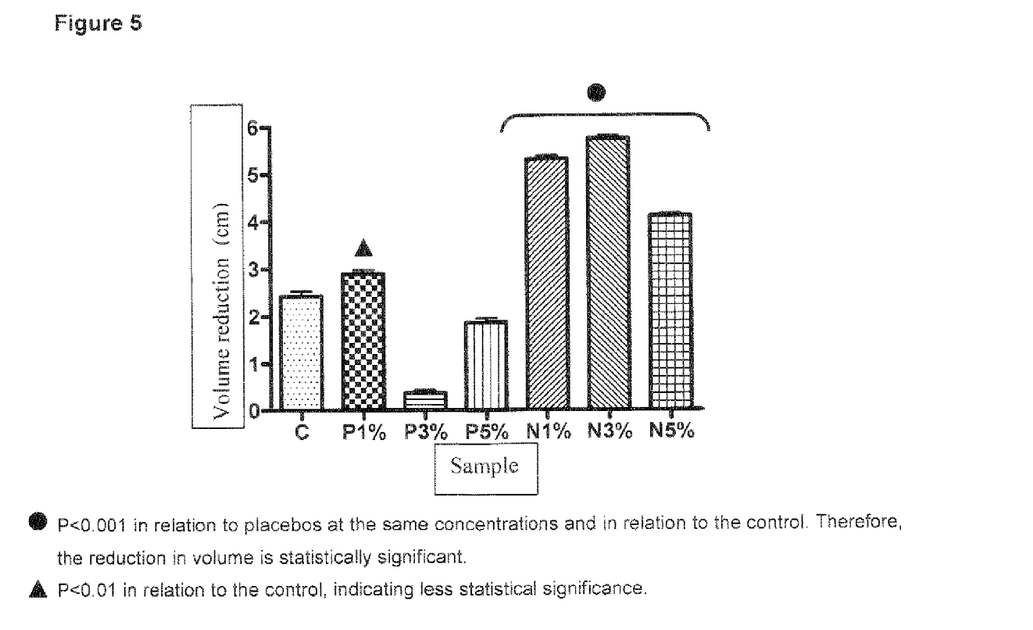
FIG. 5 shows the volume reduction of hair locks (cm) in hair treated with Control (C), Placebos (P) and Sericin cationic nanoparticles (N) in different concentrations. (P1%) aqueous placebo solution at 1%, (P3%) aqueous placebo solution at 3%, (P5%) aqueous placebo solution at 5%, (N1%) dispersion of sericin cationic nanoparticles in water at 1%, (N3%) dispersion of sericin cationic nanoparticles in water at 3%, (N5%) dispersion of sericin cationic nanoparticles in water at 5%.

FIG. 5 shows that the volume reduction promoted by the control was superior to the volume reduction promoted by the placebos at 3% and 5%. Comparing the volume reduction effect of the control to the placebo at 1%, a slight volume reduction is noted, but with low statistical significance. Proving, therefore, that the effect of cationic conditioning agents, present in the placebo formula, at the applied concentrations, is the same as water's.

Locks treated with sericin cationic nanoparticles, at different concentrations, presented great volume reduction compared to the volume reduction promoted by the placebos and the control, demonstrating the superior effect of the sericin cationic nanoparticles in reduction of hair volume.

4. Color Maintenance in Dyed Hair

In this study we evaluated the application the sericin cationic nanoparticles in hair dye formulas, in order to assess their effect in hair color maintenance, comparing the effects on locks treated with a placebo, in other words, dyed with color without the addition of sericin cationic nanoparticles.

Caucasian virgin hair locks previously bleached with hydrogen peroxide were used. The dye formulas (color no. 6.64) containing 3% of sericin cationic nanoparticles and the placebo formula (without addition of nanoparticles) were applied to the hair locks for evaluation of the proposed active agent's effect in coloring.

The studied dyes (with active ingredients and Placebo) were applied to the previously discolored, washed and dried locks.

The dye was previously mixed with a bleaching solution (hydrogen peroxide), until formation of a homogenous mixture and then it was applied on the hair, acting for 30 minutes. After this time the locks were rinsed with running water, dried at room temperature for 24 hours and submitted to colorimeter reading in Color Guide Sphere (BKY Gardner). Then these locks were washed with aqueous solution of Sodium Lauryl Ether Sulfate at 20%, dried, and submitted again to read the colorimeter. Fifteen washes were performed in total and the colorimeter measurements were taken at every 3 washes.

The principle of the color analysis technique is based on measuring the intensity of reflected light. Hair is illuminated under a light and the reflected light is recorded according to each color. The principle is based on the spectrum of reflected light in the region of visible light. The reading is based on the color system L*a*b (CIELAB). In the system, the color is set on three axes in space:

L—lightness (−100=black to 100=white)
a—color coordinate (−60 to 60=green to red)
b—color coordinate (−60 to 60=blue to yellow)

The average percentage of maintenance in these color coordinates is compared between the dyed locks with color containing sericin cationic nanoparticles and locks dyed with color without sericin cationic nanoparticles (Placebo).

Figure 7:
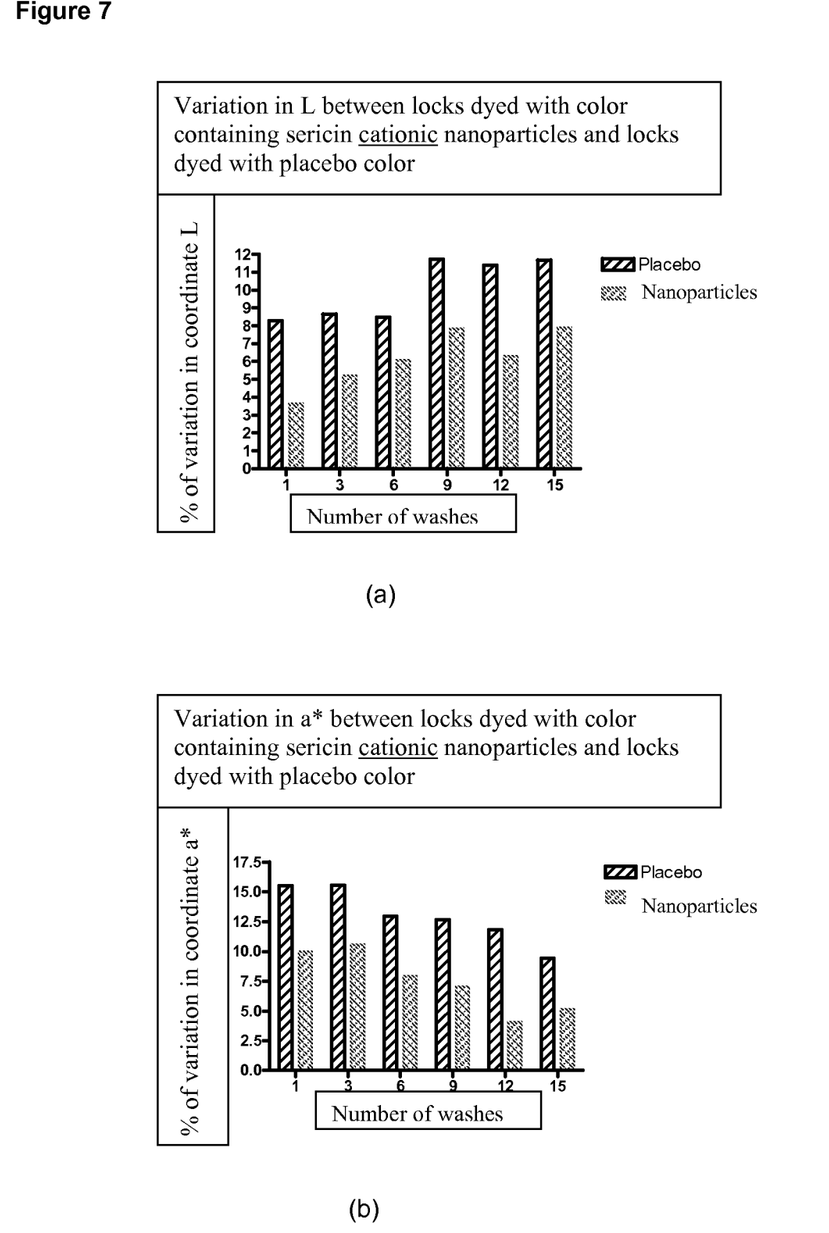
FIG. 7 shows the results the average percentage of maintenance in the color coordinates L* (a), a* (b), b* (c), between the dyed locks with color containing and without sericin cationic nanoparticles.

Analyzing the variation of luminosity (L) and chromatic coordinates a * and b * along the washes (FIG. 7), we concluded that there was a greater variation when it comes to the locks dyed with Placebo, indicating that the locks treated with color containing sericin cationic nanoparticles were more effective in maintaining the hair color along the washes.

5. Recovery of Hair Cuticles

The cationic sericin cationic nanoparticles were applied as finalizer to damaged hair locks, which were previously moistened and then dried.

The virgin hair locks and chemically damaged hair locks (after the decolorization process) were used as control in generation of images.

Figure 6:
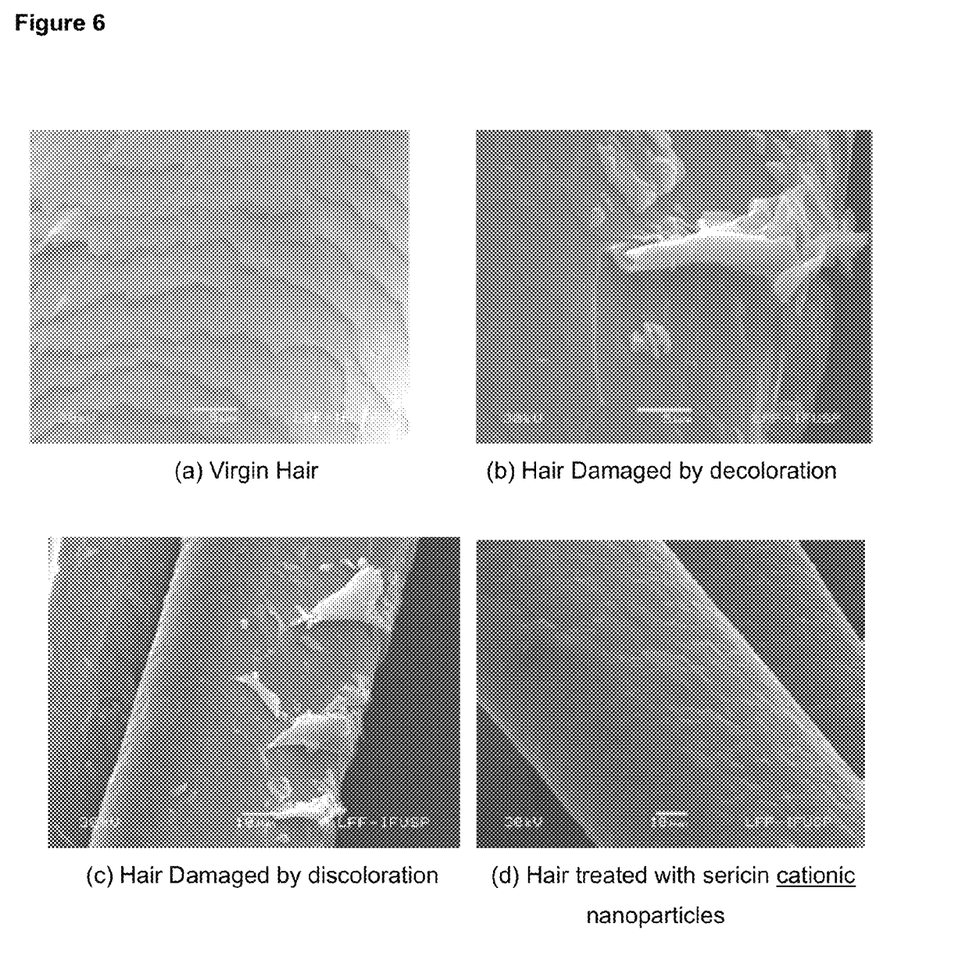
FIG. 6 shows images of virgin locks (a), locks damaged by chemical decolorant treatment (b and c) and hair treated with sericin cationic nanoparticles (d).

The evaluation of treatment effectiveness also included a comparative analysis of images obtained by Scanning Electron Microscopy. FIG. 6 shows images of hair locks damaged by chemical decolorant treatment (b and c) and virgin locks (a), both used as controls for evaluation of hair recovery after the application of sericin cationic nanoparticles. FIG. 6 shows comparative images of hair damaged by chemical decolorant treatment (c) and hair treated with sericin cationic nanoparticles (d). It can be clearly observed in FIG. 6 (d) the recovery of the hair's healthy appearance when the sericin cationic nanoparticles were applied to its surface.

FIG. 6(d) Hair treated with sericin cationic nanoparticles.

FIG. 7(a) Variation in L between locks dyed with color containing sericin cationic nanoparticles and locks dyed with placebo color;

FIG. 7(b) Variation in a* between locks dyed with color containing sericin cationic nanoparticles and locks dyed with placebo color;

FIG. 7(c) Variation in b* between locks dyed with color containing sericin cationic nanoparticles and locks dyed with placebo color.

The invention claimed is:
1. An article of manufacture, comprising sericin cationic nanoparticles dispersed in a medium containing cationic polymer, which are obtained by coating of sericin nanoparticles with at least one-cationic surfactant in a cosmetic formulation for hair care.

2. The article of manufacture according to claim 1, wherein the cosmetic formulation is selected from the group consisting of shampoos, conditioners, leave-on and leave-in combing creams.

3. The article of manufacture according to claim 1, wherein the cosmetic formulation is selected from the group consisting of formulas of hair coloration, permanent dyes, toning shampoos and decolorants.

4. The article of manufacture according to claim 1, wherein the cosmetic formulation promotes significant increase in hair gloss, volume reduction, improving softness and ease of combing, abating roughness and repairing damage.

5. The article of manufacture according to claim 1, wherein the cosmetic formulation promotes maintenance of hair coloring.

6. The article of manufacture according to claim 2, wherein the cosmetic formulation promotes significant increase in hair gloss, volume reduction, improving softness and ease of combing, abating roughness and repairing damage.

7. The article of manufacture according to claim 3, wherein the cosmetic formulation promotes maintenance of hair coloring.

\* \* \* \* \*